US009028831B2

(12) United States Patent
Arango Del Corro et al.

(10) Patent No.: US 9,028,831 B2
(45) Date of Patent: May 12, 2015

(54) MARKERS FOR SELECTING PERSONALIZED THERAPIES FOR THE TREATMENT OF CANCER

(75) Inventors: Diego Arango Del Corro, Barcelona (ES); Simó Schwartz Navarro, Barcelona (ES); John Martin Mariadason, Victoria (AU)

(73) Assignee: Fundació Institut de Recerca Hospital Universitari Vall d'Hebron, Fundació Privado, Barcelona (ES)

( * ) Notice: Subject to any disclaimer, the term of this patent is extended or adjusted under 35 U.S.C. 154(b) by 0 days.

(21) Appl. No.: 13/393,215

(22) PCT Filed: Sep. 1, 2010

(86) PCT No.: PCT/ES2010/070576
§ 371 (c)(1),
(2), (4) Date: May 16, 2012

(87) PCT Pub. No.: WO2011/027018
PCT Pub. Date: Mar. 10, 2011

(65) Prior Publication Data
US 2012/0231020 A1    Sep. 13, 2012

(30) Foreign Application Priority Data

Sep. 2, 2009    (ES) .................. 200901817

(51) Int. Cl.
*A61K 31/282* (2006.01)
*A61K 31/713* (2006.01)
*A61K 39/395* (2006.01)
*C12Q 1/68* (2006.01)

(52) U.S. Cl.
CPC ........ *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

2009/0149397 A1 *  6/2009  Ossovskaya et al. ........... 514/25

FOREIGN PATENT DOCUMENTS

| WO | 03010336 A2 | 2/2003 |
| WO | 2005098037 A1 | 10/2005 |
| WO | 2007100859 A2 | 9/2007 |
| WO | 2008112749 A1 | 9/2008 |
| WO | 2009024667 A2 | 2/2009 |
| WO | 2009099649 A1 | 8/2009 |

OTHER PUBLICATIONS

Tentori et al (Inhibition of poly(ADP-ribose) polymerase prevents irinotecan-induced intestinal damage and enhances irinotecan/temozolomide efficacy against colon carcinoma, 2006, FASEB J, vol. 29, p. E1024-E1036).*

Harris et al (Aprataxin, poly-ADP ribose polymerase 1 (PARP-1) and apurinic endonuclease 1 (APE1) function together to protect the genome against oxidative damage, 2009, vol. 18, p. 4102-4117).*
Nikolova et al (Homologous recombination protects mammalian cells from replication-associated DNA double-strand breaks arising in response to methyl methanesulfonate, DNA Repair, 2010, vol. 9, p. 1050-1063).*
L'esperance et al (International Journal of Oncology, 2006, 29:5-24).*
Reynolds et al, Molecular and Cellular Biology, 2009, 29:1354-1363; published Dec. 22, 2008.*
Fortini et al (DNA Repair, 2007, 6:398-409).*
Heale et al (Molecular Cell, 2006, 21:837-848).*
Horton et al (Cancer Research, 2008, 18:48-63).*
Douillard et al (The Lancet, 2000, 355:1041-1047).*
Allegra, C., et al., "American Society of Clinical Oncology Provisional Clinical Opinion: Testing for KRAS Gene Mutations in Patients With Metastatic Colorectal Carcinoma to Predict Response to Anti—Epidermal Growth Factor Receptor Monoclonal Antibody Therapy", "Journal of Clinical Oncology", Apr. 20, 2009, pp. 2091-2096, vol. 27, No. 12.
Allen W., et al., "Clinical Determinants of Response to Irinotecan-Based Therapy Derived from Cell LineModels", "Clin Cancer Res", Oct. 15, 2008, pp. 6647-6655, vol. 14, No. 20.
Aschele, C., et al., "Thymidylate Synthase expression as a predictor of clinical repsone to fluoropyrimidine-based chemotherapy in advanced colorectal cancer", "Cancer Treatment Reviews", 2002, pp. 27-47, vol. 28.
Braun, M., et al., "Predictive Biomarkers of Chemotherapy Efficacy in Colorectal Cancer: Results From the UK MRC Focus Trial", "Journal of Clinical Oncology", Jun. 1, 2008, pp. 2690-2698 and Errata p. 43-63, vol. 26, No. 16.
Chua, Y., et al., "Recent Data with AntiEpidermal Growth Factor Receptor Antibodies and Irinotecan in Colon Cancer", "Clinical Colorectal Cancer", Oct. 2005, pp. S81-S88, vol. 5 Suuplement 2.
Cunningham, D., et al., "Cetuximab Monotherapy and Cetuximab plus Irinotecan in Irinotecan-Refractory Metastatic Colorectal Cancer", "N. Engl. J. Med.", Jul. 22, 2004, pp. 337-345, vol. 351, No. 4.
Dopeso, H., et al., "Aprataxin Tumor Levels Predict Response of Colorectal Cancer Patients to Irinotecan-based Treatment", "Clin Cancer Res", Apr. 15, 2010, pp. 2375-2382, vol. 16, No. 8.
Douillard, J., et al., "Irinotecan combined with fluorouracil compared with fluorouracil alone as first-line treatement for metastatic colorectal cancer: a multicentre randomised trial", "The Lancet", Mar. 25, 2000, pp. 1041-1047, vol. 355.
Emmanouilides, C., et al., "Front-line Bevacizumab in combination with Oxaliplatin, Leucovorin and 5-Fluorouracil (Folfox) in patients with metastatic colorectal cancer: a multicenter phase II study", "BMC Cancer", May 30, 2007, pp. 17, vol. 7 Article No. 91.

(Continued)

*Primary Examiner* — Sean Aeder
*Assistant Examiner* — Julie Wu
(74) *Attorney, Agent, or Firm* — Hultquist, PLLC; Mary B. Grant (57) ABSTRACT

The invention relates to the identification of aprataxin (APTX) expression levels as a marker for the response to topoisomerase I inhibitor-based therapies in patients with cancer and, more particularly, colon cancer. The invention also relates to methods for treating patients with cancer who have low APTX expression levels by means of administering a topoisomerase I inhibitor to said patients.

6 Claims, 2 Drawing Sheets

(56) References Cited

OTHER PUBLICATIONS

Goldberg, R., et al., "A Randomized Controlled Trial of Fluorouracil Plus Leucovorin, Irinotecan, and Oxaliplatin Combinations in Patients With Previously Untreated Metastatic Colorectal Cancer", "Journal of Clinical Oncology", Jan. 1, 2004, pp. 2330, vol. 22, No. 1.

Hurwitz, H., et al., "Bevacizumab plus Irinotecan, Fluorouracil, and Leucovorin for Metastatic Colorectal Cancer", "N. Engl. J. Med.", Jun. 3, 2004, pp. 2335-2342, vol. 350.

Iqbal, S., et al., "Determinants of Prognosis and Response to Therapy in Colorectal Cancer", "Current Oncology Reports", Mar. 2001, pp. 102-108, vol. 3.

Mariadason, J., et al., "Gene Expression Profiling-Based Prediction of Response of Colon Carcinoma Cells to 5-Fluorouracil and Camptothecin", "Cancer Research", Dec. 15, 2003, pp. 8791-8812, vol. 63.

Moertel, C., et al., "Fluorouracil plus Levamisole as Effective Adjuvant Therapy after Resection of Stage III Colon Carcinoma: A Final Report", "Annals of Internal Medicine", Mar. 1, 1995, pp. 321326, vol. 122, No. 5.

Parkin, D., et al., "Global Cancer Statistics, 2002", "CA Cancer J. Clin.", 2005, pp. 74-108, vol. 55.

Pavillard, V., et al., "Cellular Parameters Predictive of the Clinical Response of Colorectal Cancers to Irinotecan. A Preliminary Study", "Anticancer Research", 2004, pp. 579-586, vol. 24.

Petrelli, N., et al., "The Modulation of Fluorouracil With Leucovorin in Metastatic Colorectal Carcinoma: A Prospective Randomized Phase III Trial", "Journal of Clinical Oncology", Oct. 1989, pp. 1419-1426, vol. 7, No. 10.

Raponi, M., et al., "A 2-gene classifier for predicting response to the farnesyltransferase inhibitor tipifarnib in acute myeloid leukemia", "Blood", Mar. 1, 2008, pp. 2589-2596, vol. 111, No. 5.

Saltz, L., et al., "Irinotecan Plus Fluorouracil and Leucovorin for Metastatic Colorectal Cancer", "N. Engl. J. Med.", Sep. 28, 2000, pp. 905-914, vol. 343, No. 13.

Shirota, Y., et al., "ERCC1 and Thymidylate Synthase mRNA Levels Predict Survival for Colorectal Cancer Patients Receiving Combination Oxaliplatin and Fluorouracil Chemotherapy", "Journal of Clinical Oncology", Dec. 1, 2001, pp. 4298-4304, vol. 19, No. 23.

Vallboehmer, D., et al., "Molecular determinants of irinotecan efficacy", "Int. J. Cancer", 2006, pp. 2435-2442, vol. 119.

Note: For the non-patent literature citations that no month of publication is indicated, the year of publication is more than 1 year prior to the effective filing date of the present application.

Lundin, C., et al., "Methyl Methanesulfonate (MMS) Produces Heat-Labile DNA Damage But No Detectable In Vivo DNA Double-Strand Breaks", "Nucleic Acids Research", Jul. 11, 2005, pp. 3799-3811, vol. 33, No. 12.

Magrini, R., et al, "Cellular Effects of CPT-11 on Colon Carcinoma Cells: Dependence on p53 and hMLH1 Status", "Int. J. Cancer", Sep. 1, 2002, pp. 23-31, vol. 101.

Park, S., et al., "X-ray Repair Cross-Complementing Gene I Protein Plays an Important Role in Camptothecin Resistance", "Cancer Research", Jan. 15, 2002, pp. 459-465, vol. 62.

Clements, P., et al., "The ataxia-oculomotor apraxia 1 gene product has a role distinct from ATM and interacts with the DNA strand break repair proteins XRCC1 and XRCC4", "DNA Repair", Aug. 17, 2004, pp. 1493-1502, vol. 3.

\* cited by examiner

MARKERS FOR SELECTING PERSONALIZED THERAPIES FOR THE TREATMENT OF CANCER

CROSS-REFERENCE TO RELATED APPLICATIONS

This is a U.S. national phase under the provisions of 35 U.S.C. §371 of International Patent Application No. PCT/ES10/70576 filed Sep. 1, 2010, which in turn claims priority of Spainish Patent Application No. P200901817 filed Sep. 2, 2009. The disclosures of such international patent application and Spainish priority patent application are hereby incorporated herein by reference in their respective entireties, for all purposes.

TECHNICAL FIELD OF THE INVENTION

The invention is encompassed in the field of methods for personalized medicine and, specifically, within the field of methods for selecting therapies suitable for treating colorectal cancer based on the expression levels of markers in samples isolated from the patient.

BACKGROUND OF THE INVENTION

Colorectal cancer accounts to a million of new cases and more than 500,000 deaths worldwide annually and the treatment options available are far from being optimum (Parkin D M, et al., CA Cancer J Clin 2005; 55: 74-108). The curative treatment of these patients involves surgery and/or chemotherapy. Palliative chemotherapy is commonly administered for patients with advanced disease and it can significantly improve the patients' quality of life and overall survival. Pyrimidine analogue, 5-fluorouracil (5-FU), has been the method of reference for treating colorectal cancer for over four decades. However, only about 20% of patients with colorectal cancer benefit from 5-FU treatment, be it in the context of adjuvant or advanced disease treatment (Moertel C G, et al., Ann Intern Med 1995; 122: 321-6; Petrelli N, et al., J Clin Oncol 1989; 7: 1419-26). More recently, additional chemotherapeutic agents for treating these patients have been approved and are now commonly used. These include the topoisomerase I inhibitor irinotecan, the platinum compound oxaliplatin and monoclonal antibodies directed against epidermal growth factor receptor (EGFR) and vascular endothelial growth factor (VEGF). These new agents have increased the percentage of patients with advanced disease with an objective response up to approximately 50% and a modest but significant improvement in their overall survival (Douillard J Y, et al., Lancet 2000; 355: 1041-7; Goldberg R M, et al., J Clin Oncol 2004; 22: 23-30; Cunningham D, et al., N Engl J Med 2004; 351: 337-45; Hurwitz H, et al., N Engl J Med 2004; 350: 2335-42; Saltz L B, et al., N Engl J Med 2000; 343: 905-14).

Based on the lack of response from half of the treated patients and the modest survival improvement of those who do respond, it is obvious that additional chemotherapeutic agents are urgently needed. Furthermore, since the different chemotherapeutic agents available today are only effective in overlapping subsets of patients, it would be very advantageous to have markers capable of distinguishing the patients who will most probably respond to each of the different agents, in an attempt to improve the clinical treatment of these patients using a more personalized approach for chemotherapeutic treatment. A number of molecular markers capable of predicting the probability of responding to these chemotherapeutic agents have been described in the last decades. The tumor expression levels of the 5-FU's target thymidylate synthase (TS), the nucleotide excision repair gene ERCC1 (excision repair cross complementing-group 1) or the mutation stage of KRAS oncogene can, for example, predict the response of 5-FU, oxaliplatin and cetuximab, respectively (Allegra C J, et al., J Clin Oncol 2009; Aschele C, et al., Cancer Treat Rev 2002; 28: 27-47; Shirota Y, et al, J Clin Oncol 2001; 19: 4298-304).

However, there has been very little progress in identifying markers capable of predicting the response to irinotecan-based treatment.

SUMMARY OF THE INVENTION

In a first aspect, the invention relates to a method for determining the response of a patient with a tumor to a topoisomerase I inhibitor which comprises comparing the APTX expression levels determined in a sample isolated from said patient with respect to a reference value, where low APTX levels are indicative of a good response to topoisomerase I inhibitor.

In another aspect, the invention relates to a method for selecting a therapy for a patient with colorectal cancer which comprises determining the APTX expression levels in a sample isolated from said patient with respect to a reference value, where
(i) if the APTX expression levels with respect to said reference value are low, the patient is selected for treatment with a topoisomerase I inhibitor and/or
(ii) if the APTX expression levels with respect to said reference value are high, the patient is selected for treatment with an agent selected from the group of a platinum-based agent, an EGFR inhibitor, a VEGF inhibitor or a combination of one or more of the above.

In a third aspect, the invention relates to the use of a topoisomerase I inhibitor for the preparation of a drug for treating colorectal cancer in a patient where the patient is selected for said treatment if low APTX expression levels with respect to a reference value are detected in a sample isolated from said patient.

In a fourth aspect, the invention relates to the use of a platinum-based agent, an EGF inhibitor, a VEGF inhibitor or a combination of one or more of the above or for the preparation of a drug for treating the colorectal cancer where the patient is selected for said treatment if high APTX expression levels with respect to a reference value are detected in a sample isolated from said patient.

In a fifth aspect, the invention relates to a composition comprising a topoisomerase I inhibitor and an APTX inhibitor.

In a sixth aspect, the invention relates to the use of a composition comprising a topoisomerase I inhibitor and an aprataxin inhibitor for the preparation of a drug for treating the cancer.

BRIEF DESCRIPTION OF THE DRAWINGS

FIG. 1 shows that the deletion of APTX sensitizes to CTP. Exposing the parental cells DT40 to 15 and 25 nM CPT for hours caused modest apoptosis induction. However, the directed inactivation of APTX caused a significantly increased apoptosis induction in response to the treatment with CPT. The reintroduction of APTX in knock-out cells DT40 fully reestablished the resistant phenotype of the parental cells DT40.

DETAILED DESCRIPTION OF THE INVENTION

The authors of the present invention have surprisingly observed that the aprataxin expression levels are associated with the response of a patient with cancer to the treatment with irinotecan. Specifically, as observed in Example 2 of the present invention, the patients who showed low aprataxin levels or in whom this molecule was undetectable showed a longer time to progression and higher survival in response to the treatment with irinotecan than the patients with moderate or high aprataxin levels. The patients with a low probability of responding to irinotecan-based treatment are ideal candidates for receiving treatment with available alternative agents such as oxaliplatin, cetuximab and/or bevacizumab.

Method for Determining the Response to Topoisomerase Inhibitor-Based Therapy

In a first aspect, the invention relates to a method (hereinafter first method of the invention) for determining the response of a patient with a tumor to a topoisomerase I inhibitor which comprises comparing the APTX expression levels determined in a sample isolated from said patient with respect to a reference value, where low APTX levels are indicative of a good response to topoisomerase I inhibitor.

The expression "determining the response of a patient" refers to the assessment of the results of a therapy in a patient with cancer in response to a therapy based on using topoisomerase I inhibitors. The use of the biomarkers of the invention to monitor the efficacy of a treatment can also be applied to methods for selecting and screening drugs with potential anti-tumor activity. This process comprises a) administrating to the subject (preferably an animal) the drug to be studied; b) taking biological samples from the animal at different points of the study (before, during and/or after administration) and determining the levels of marker according to the present invention; and c) comparing the determinations made in the samples obtained in the different phases of treatment and comparing them to control animals, for example, untreated animals.

The cancer to be treated in the context of the present invention can be any type of cancer or tumor. These tumors or cancer include, but are not limited to, blood cancer (for example leukemia or lymphoma), neural tumors (for example astrocytoma or glioblastoma), melanoma, breast cancer, lung cancer, head and neck cancer, gastrointestinal tumors (for example stomach, pancreatic or colorectal cancer), liver cancer (for example hepatocellular carcinoma), renal cell cancer, urogenital tumors (for example ovary cancer, vaginal cancer, cervical cancer, bladder cancer, testicular cancer, prostate cancer), bone tumors and vascular tumors. Therefore, in a particular embodiment, the cancer disease to be treated or prevented is colorectal cancer.

As used herein, the term "colorectal cancer" (CRC) includes any type of colon, rectum and appendix neoplasm and refers both to early and late adenomas and to carcinoma as well as to hereditary, familial or sporadic cancer. Hereditary CRC includes those syndromes which include the presence of polyps, such as the hamartomatous polyposis syndromes and the most well-known, familial adenomatous polyposis (FAP) as well as nonpolyposis syndromes such as hereditary nonpolyposis colorectal cancer (HNPCC) or Lynch syndrome I. The present invention also contemplates the treatment of colorectal cancer in its different stages such as stages A, B, C1, C2 and D according to Dukes' classification, stages A, B1, B2, B3, C1, C2, C3 and D according to the Astler-Coller classification, stages TX, T0, Tis, T1, T2, T3, NX, N0, N1, N2, MX, M0 and M1 according to the TNM system as well as stages 0, I, II, III and IV according to the AJCC (American Joint Committee on Cancer) classification.

As used herein, the term "subject" or "patient" refers to all the animals classified as mammals and includes, but is not restricted to, domestic and farm animals, primates and humans, for example, human beings, non-human primates, cows, horses, pigs, sheep, goats, dogs, cats, or rodents. The subject is preferably a male or female human of any age or race.

The terms "aprataxin or APTX" are used interchangeably in the present invention and refer to a protein belonging to a superfamily called the HIT domain family formed by proteins such as nucleotide binding protein (HINT), fragile histidine triad (FHIT), galactose-1-phosphate uridyl transferase (GALT), IPR011151 and DcpS. The HIT domain is characterized by having a consensus sequence of the HXHXHXX type where X is a hydrophobic amino acid. Aprataxin additionally contains a N-terminus Forkhead-associated (FHA) domain which is capable of binding to phosphoproteins and a C-terminus region which is a zinc-finger type putative DNA-binding domain. The aprataxin which can be determined according to the present invention preferably corresponds to the human protein identified in the NCBI database with the accession number AAQ74130 (in the version of 29 Sep. 2004), although it can also refer to the rat protein (accession number NP 683687 in the NCBI database in the version of 11 Feb. 2008), mouse protein (accession number AAH21872 in the NCBI database in the version of 30 Jan. 2008), swine protein (accession number NP_998899 in the NCBI database in the version of 18 Nov. 2006), dog protein (accession number NP_001003355 in the NCBI database in the version of 14 Jun. 2007), cow protein (accession number NP 872595 in the NCBI database in the version of 2 Nov. 2008), horse protein (accession number XP_001917754 in the NCBI database in the version of 11 Jun. 2008) and the like.

As used herein, the term "aprataxin" does not only include the exact sequences defined above but it also includes aprataxin variants in which one or more of the amino acid residues are substituted with a conserved or non-conserved amino acid residue (preferably a conserved amino acid residue) and such substituted amino acid residue may or may not be an amino acid residue encoded by the genetic code, or (ii) variants comprising an insertion or a deletion of one or more amino acids. The variants according to the invention preferably have at least 50%, at least 60%, at least 70%, at least 80%, at least 90%, at least 91%, at least 92%, at least 93%, at least 94%, at least 95%, at least 96%, at least 97%, at least 98% or at least 99% sequence identity with the APTX amino acid sequence. The degree of identity between the variants and the specific aprataxin sequences defined above is determined using algorithms and computer processing which are widely known by the persons skilled in the art. The identity between two amino acid sequences is preferably determined using the BLASTP algorithm [BLAST Manual, Altschul, S., et al., NCBI NLM NIH Bethesda, Md. 20894, Altschul, S., et al., J. Mol. Biol. 215: 403-410 (1990)].

To carry out the first method of the invention, it is necessary to obtain a sample from the subject under study. As used herein, the term "sample" refers to any sample which can be obtained from the patient, such as a biopsy sample, tissue sample, cell sample or fluid sample (serum, saliva, semen, sputum, cerebrospinal fluid (CSF), tears, mucus, sweat, milk, brain extracts and the like). In a particular embodiment, said sample is a tissue sample or a part thereof, preferably a tumor tissue sample or a part thereof. Said sample can be obtained by means of conventional methods, for example, biopsy, using methods well known by the persons skilled in the related medical techniques. The methods for obtaining a biopsy sample include dividing a tumor into large pieces, or microdissection or other cell separation methods known in the art. The tumor cells can additionally be obtained by means of fine needle aspiration cytology. To simplify sample storage and handling, they can be fixed in formalin and embedded in paraffin or first frozen and then embedded in a cryosolidifiable medium, such as OCT compound, by means of immersion in a highly cryogenic medium that allows quick freezing.

The APTX expression levels, as understood by the person skilled in the art, can be determined by measuring the levels of APTX encoding mRNA or by measuring the levels of APTX protein.

Therefore, in a particular embodiment of the invention, the APTX expression levels are determined by measuring the expression levels of the mRNA encoded by the APTX gene. For this purpose, the biological sample can be treated to physically and mechanically break down the tissue or cell structure to release the intracellular components into an aqueous or organic solution to prepare the nucleic acids for additional analyses. The nucleic acids are extracted from the sample by means of commercially available methods known by the person skilled in the art. The RNA is then extracted from frozen or fresh samples by means of any of the typical methods in the art, for example Sambrook, J., et al., 2001 Molecular Cloning, a Laboratory Manual, 3rd ed., Cold Spring Harbor Laboratory Press, N.Y., Vol. 1-3. Care is preferably taken to prevent the RNA from degrading during the extraction process.

In a particular embodiment, the expression level can be determined using the mRNA obtained from a tissue sample fixed in formalin, embedded in paraffin. The mRNA can be isolated from a pathological sample on file or a biopsy sample which is first deparaffinized. An exemplary deparaffinization method involves washing the sample in paraffin with an organic solvent, such as xylene. The deparaffinized samples can be rehydrated with an aqueous solution of a lower alcohol. The suitable lower alcohols include, for example, methanol, ethanol, propanols, and butanols. The deparaffinized samples can, for example, be rehydrated with successive washings with lower alcohol solutions of decreasing concentrations. Alternatively, the sample is deparaffinized and rehydrated simultaneously. The sample is then lysed and the RNA is extracted from the sample.

While all gene expression profile determination techniques (RT-PCR, SAGE, expression microarrays or TaqMan) are suitable for use in performing the previous aspects of the invention, the expression levels of mRNA are usually determined by means of reverse transcription polymerase chain reaction (RT-PCR). In a particular embodiment, the expression levels of mRNA of APTX are determined by means of quantitative PCR, preferably real time PCR. The detection can be carried out in individual samples or in tissue microarrays.

It is possible to compare the expression levels of mRNA of interest in the samples to be assayed with the expression of a control RNA to normalize the values of mRNA expression among the different samples. As used herein, "control RNA" refers to a RNA the expression levels of which do not change or only change in limited amounts in tumor cells with respect to non-tumorigenic cells. The control RNA is preferably mRNA derived from housekeeping genes and which encodes proteins which are constitutively expressed and which perform essential cell functions. Examples of housekeeping genes for use in the present invention include β-2-microglobulin, ubiquitin, 18-S ribosomal protein, cyclophilin, GAPDH and actin. In a preferred embodiment, the control RNA is β-actin mRNA. In one embodiment, the quantification of the relative gene expression is calculated according to the comparative Ct method using β-actin as endogenous control and commercial RNA controls as calibrators. The final results are determined according to the formula $2^{-(\Delta Ct\ of\ the\ sample - \Delta Ct\ of\ the\ calibrator)}$, where the $\Delta CT$ values of the calibrator and the sample are determined by subtracting the target gene CT value from the β-actin gene value.

Alternatively, in another particular embodiment, the APTX expression levels can be determined by measuring either the level of said protein or the level of variants thereof.

The expression levels of the proteins can be determined by means of immunological techniques such as for example, ELISA, immunoblot, immunofluorescence or immunohistochemical techniques. Immunoblot is based on the detection of proteins previously separated by means of gel electrophoresis in denaturing conditions and immobilized in a membrane, generally nitrocellulose membrane, by means of incubation with a specific antibody and a development system (for example, chemoluminescence). Analysis by means of immunofluorescence requires the use of an antibody specific for the target protein for analyzing the expression. ELISA is based on the use of antigens or antibodies labeled with enzymes such that the conjugates formed between the target antigen and the labeled antibody result in the formation of enzymatically active complexes. Given that one of the components (the antigen or the labeled antibody) are immobilized on a support, the antigen-antibody complexes are immobilized on the support and can thus be detected by means of adding a substrate which is converted by the enzyme into a product which is detectable by means of, for example, spectrophotometry or fluorometry.

When an immunological method is used, any antibody or reagent which is known to bind to the target proteins with high affinity can be used for detecting the amount of target proteins. However the use of an antibody, for example polyclonal sera, hybridoma supernatants or monoclonal antibodies, antibody fragments, Fv, Fab, Fab' and F(ab')2, scFv, diabodies, triabodies, tetrabodies and humanized antibodies, is preferred.

In addition, the expression levels of proteins can be determined by means of immunohistochemical techniques well known in the state of the art. To carry out the determination by means of immunohistochemical technique, the sample can be a fresh sample, a frozen sample or a sample embedded in paraffin and fixed using a protective agent of the formalin type. For the immunohistochemical determination, the sample is stained with an aprataxin specific antibody and the frequency of cells which have been stained and the staining intensity are determined. A total value and an expression indicative value, which are calculated depending on the frequency of stained cells (value which varies between 0 and 4) and on the intensity in each of the stained cells (value variable between and 4) are typically assigned to the sample. Typical criteria for assigning expression values to the samples have been described in detail, for example, in Handbook of Immunohistochemistry and In Situ Hybridization in Human Carcinomas, M. Hayat Ed., 2004, Academic Press. Additionally, immunohistochemical techniques allow identifying which type of cells from those present in the cancerous tissue are the ones having altered marker expression levels. The immunohistochemical detection is preferably carried out in parallel with cell samples which serve as positive marker and as negative marker and healthy tissues of the same origin as the tumor under analysis can be used as a reference. It is also common to use a background control.

In those cases in which a large number of samples is to be analyzed (for example, when several samples from one and the same patient or samples from different patients are to be analyzed), the use of arrays and/or automated methods is possible. In one embodiment, the use of tissue microarrays (TMA) which can be obtained using different techniques is possible. The samples forming part of the microarrays can be analyzed in a different manner including immunohistochemical techniques, in situ hybridization, in situ PCR, RNA or DNA analysis, morphological inspection and combinations of any of the above. Methods for processing tissue microarrays have been described, for example, in Konenen, J. et al., (Nat. Med. 1987, 4:844-7). Tissue microarrays are prepared from cylindrical cores of 0.6 to 2 mm in diameter from tissue samples embedded in paraffin and then embedded again in a single recipient block. The tissue from several samples can thus be inserted in a single paraffin block.

The determination of APTX expression levels needs to be correlated with the reference values which correspond to the median value of the APTX expression levels measured in a collection of tumor tissues in biopsy samples from subjects with cancer. Said reference sample is typically obtained by combining equal amounts of samples from a population of subjects. The typical reference samples will generally be obtained from subjects who are clinically well documented and in whom the disease is well characterized by some of the common methods (rectal exam, fecal occult blood test, sigmoidoscopy, colonoscopy, biopsy, determination of tumor markers such as the carcinoembryonic antigen, ultrasound, CAT scan, nuclear magnetic resonance, positron emission tomography). In such samples, the normal (reference) concentrations of the biomarker can be determined, for example by providing the mean concentration over the reference population. When the reference concentration of the marker is determined, several considerations are taken into account. Such considerations include the type of sample involved (for example tissue or CSF), age, weight, sex, general physical condition of the patient and the like. For example, equal amounts of a group of at least 2, at least 10, at least 100 to preferably more than 1000 subjects, preferably classified according to the previous considerations, for example of several age categories are taken as a reference group. The collection of samples from which the reference value is derived will preferably consist of subjects with the same type of cancer as the patient under study.

Once this median value is established, the level of this marker expressed in tumor tissues of patients can be compared with this median value, and thus be assigned to the "reduced" or "increased" expression level. Due to the variability among subjects (for example, aspects concerning age, race, etc.), it is very difficult (if not virtually impossible) to establish absolute reference values of APTX expression. Therefore, in a particular embodiment, the reference values for "increased" or "reduced" expression of APTX expression are determined by calculating the percentiles by conventional means which involves assaying one or several samples isolated from normal subjects in whom the disease is well documented by any of the methods mentioned above for APTX expression levels. The "reduced" APTX levels can then preferably be assigned to samples in which APTX expression levels are equal to or less than the $50^{th}$ percentile in the normal population, including, for example, expression levels equal to or less than the $60^{th}$ percentile in the normal population, equal to or less than the $70^{th}$ percentile in the normal population, equal to or less than the $80^{th}$ percentile in the normal population, equal to or less than the $90^{th}$ percentile in the normal population, and equal to or less than the $95^{th}$ percentile in the normal population. The "increased" APTX levels can then preferably be assigned to samples in which the APTX expression levels are equal to or greater than the $50^{th}$ percentile in the normal population, including, for example, expression levels equal to or greater than the $60^{th}$ percentile in the normal population, equal to or greater than the $70^{th}$ percentile in the normal population, equal to or greater than the $80^{th}$ percentile in the normal population, equal to or greater than the $90^{th}$ percentile in the normal population, and equal to or greater than the $95^{th}$ percentile in the normal population.

As used herein, the expression "low APTX expression levels" refers to APTX levels less than those found in a reference sample. It can be particularly considered that a sample has low APTX expression levels when the expression levels in the reference sample are at least 1.1 times, 1.5 times, 5 times, 10 times, 20 times, 30 times, 40 times, 50 times, 60 times, 70 times, 80 times, 90 times, 100 times or even more with respect to the sample isolated from the patient.

As used herein, the expression "topoisomerase I inhibitor" includes any compound capable of inhibiting topoisomerase I activity determined by means of any of the relaxation assays known in the art such as those described by Liu et al. (Proc. Natl. Acad. Sci. USA, 1981, 76:3487-3491) as well as any compound capable of inhibiting the nuclease activity of topoisomerase I such as those described by Hsiang et al. (J. Biol. Chem., 1985, 260:14873-14878).

Examples of topoisomerase I inhibitors include, without limitation, topotecan, gimatecan, irinotecan, camptothecin, SN and its analogues, 9-nitrocamptothecin and the macromolecular camptothecin conjugate PNU-166148 (compound A1 in WO9917804); 10-hydroxycamptothecin acetate salt; idarubicin hydrochloride; irinotecan hydrochloride; teniposide; topotecan hydrochloride; doxorubicin; epirubicin hydrochloride; mitoxantrone hydrochloride and daunorubicin hydrochloride. Irinotecan can be administered, for example, in the form in which it is marketed, i.e., under the trademark CAMPTOSAR. Topotecan can be administered, for example, in the form in which it is marketed, i.e., under the trademark HYCAMTIN.

The terms "good" and "bad" as used in the context of an invention to refer to the response of a patient to the treatment with topoisomerase I inhibitors, refers to the fact that the patient will show a favorable response or an unfavorable response to the treatment. The person skilled in the art will see that the determination of the response to the treatment will not be 100% correct for the patients analyzed. Nevertheless, the determination of the response is intended to be correct for a statistically significant fraction of the patients. The determination of whether a response is statistically significant can be carried out using statistical evaluation tools such as confidence intervals, determination of the p value, Student's t-test, Mann-Whitney test, etc. The way of putting these tools into practice is described in detail in, for example, Dowdy and Wearden, Statistics for Research, John Wiley & Sons, New York 1983. The preferred confidence intervals are at least 50%, at least 60%, at least 70%, at least 80%, at least 90%, at least 95%. The p values are preferably 0.2, 0.1, 0.05.

The determination of the response of a patient to a specific therapy can be determined using any assessment criterion used in oncology and known by the person skilled in the art. The assessment parameters useful for describing the progression of a disease include:

- disease-free progression which, as used herein, describes the ratio of subjects in complete remission who have not had disease relapse during the time period under study;
- objective response, which, as used in the present invention, describes the ratio of people treated in whom a complete or partial response is observed;
- tumor control, which, as used in the present invention, relates to the ratio of people treated in whom a complete response, partial response, minor response or stable disease ≥6 months is observed;
- progression-free survival which, as used herein, is defined as the time from the beginning of the treatment until the first measurement of cancer growth.
- progression-free survival of six months or "PFS6" rate which, as used herein, relates to the percentage of people who are progression-free in the first six months after the beginning of the therapy
- median survival which, as used herein, relates to the time in which half of the patients enrolled in the study are still alive, and
- time to progression, as used herein, relates to the time from the moment the disease is diagnosed (or treated) until the disease worsens.

In a preferred embodiment, the response of a patient is determined by means of a parameter selected from time to progression and survival.

Methods for Personalized Therapy and for Designing Personalized Therapy

The authors of the present invention have also showed that high aprataxin levels allows identifying patients with a low probability of responding to a topoisomerase I inhibitor-based treatment (see Example 2 of the present invention), therefore these patients would be the ideal candidates for receiving treatment with compounds which are commonly used in those cases in which the topoisomerase I inhibitor has not produced the result such as has been described by Cunningham et al. (N. Engl. J. Med. 2004, 351:337-45) and by Hurwitz et al. (N. Engl. J. Med., 2004, 3:2335-42). Compounds of this type include, without limitation, platinum-based compounds, EGFR inhibitors or VEGF inhibitors.

Therefore, in another aspect, the invention relates to a method (hereinafter second method of the invention) for selecting a therapy for a patient with colorectal cancer which comprises determining in a sample isolated from said patient the APTX expression levels with respect to a reference value, where (i) if the APTX expression levels with respect to said reference value are low, the patient is selected for treatment with a topoisomerase I inhibitor and/or (ii) if the APTX expression levels with respect to said reference value are high, the patient is selected for treatment with an agent selected from the group of a platinum-based agent, an EGFR inhibitor, a VEGF inhibitor or a combination of one or more of the above.

The terms and expressions "patient", "colorectal cancer", "sample", "determination of levels", "aprataxin", "topoisomerase I inhibitor", "high levels" and "low levels", "reference value" have been described in detail in relation to the first method of the invention and are equally applicable to the second method of the invention.

As used herein, the term "platinum-based agent" refers to any compound comprising at least one platinum atom and which is capable of binding to and crosslinking with DNA, thus activating the DNA repair pathways and triggering apoptosis. Platinum-based compounds include, without limitation, carboplatin, cisplatin [cis-diamminedichloroplatinum, (CDDP)], oxaliplatin, iproplatin, nedaplatin, triplatin tetranitrate, tetraplatin, satraplatin, and the like.

As used herein, the term "EGFR inhibitor" refers to any molecule capable of completely or partially inhibiting EGFR-mediated signaling either by means of inhibiting the binding of EGF to the extracellular region of the receptor or by means of inhibiting the tyrosine kinase activity located in the intracellular region of EGFR. EGFR inhibitors can be identified using methods based on measuring the tyrosine kinase activity in the presence of the so-called inhibitor such as that described in Hsu et al. (J. Biol. Chem., 1991, 261:21105-21112) or the ELISA-based methods such as that described in Varkondi et al. (J. Recept. Signal. Transduct. Res. 2005; 25:45-56). Alternatively, it is possible to identify EGFR inhibitors using methods based on the capacity of inhibiting the proliferation of tumor cells overexpressing EGFR in soft agar such as has been described by Hudziak et al. (Mol. Cell. Biol., 1989, 9:1165-1172) and Lupu, R. et al. (Science, 1990, 249:1552-1555).

Examples of EGFR inhibitory agents include both antibodies and small molecules with EGFR-binding capacity. Examples of EGFR extracellular domain-specific antibodies include the monoclonal antibodies 579 (ATCC CRL HB 8506), 455 (ATCC CRL HB8507), 225 (ATCC CRL 8508), 528 (ATCC CRL 8509) (see the U.S. Pat. No. 4,943,533 to Mendelsohn et al.) as well as variants thereof such as chimeric 225 (C225) and humanized 225 (H225) antibodies (see WO 96/40210 to Imclone Systems Inc.), antibodies capable of binding to type II mutant EGFR (see U.S. Pat. No. 5,212, 290); EGFR-binding chimeric and humanized antibodies such as those described in U.S. Pat. No. 5,891,996; and EGFR-binding human antibodies (see WO98/50433, Abgenix), (Avastin), 2C3, HuMV833, cetuximab (Erbitux®), panitumumab (Vectibix®), nimotuzumab (TheraCim®), matuzumab, zalutuzumab, mAb 806 or IMC-1 1F8. Examples of EGFR tyrosine kinase activity inhibitors include ZD1839 or Gefitinib (IRESSA™; Astra Zeneca), CP-358774 (TARCEVA™; Genentech/OSI) and AG1478, AG1571 (SU 5271; sugen), erlotinib (Tarceva), sutent (sunitinib), lapatinib, sorafenib (nexavar), vandetanib, axitinib, bosutinib, cedivanib, dasatinib (sprycel), lestaurtinib, and/or ARQ1 97. In a preferred embodiment, the EGFR inhibitor is cetuximab.

As used herein, the term "VEGF inhibitor" refers to a compound which inhibits the activity or production of VEGF and which results in a reduction of signaling via the VEGF-VEGF receptor pathway. VEGF inhibitors can be identified using methods based on determining the proliferative capacity of human vascular endothelial cells such as has been described by Kendall and Thomas (Proc. Natl: Acad. Sci. USA, 1993, 90:10705-10709) or based on determining the proliferative capacity of retinal endothelial cells such as has been described by Aiello et al., (Proc. Natl: Acad. Sic. USA, 1995, 92:10457-10461).

VEGF inhibitory compounds include, without limitation, small organic molecules, VEGF-specific antibodies or antibody fragments, peptides, antisense nucleic acids, iRNA and ribozymes capable of inhibiting VEGF expression. Nucleic acids with VEGF inhibiting capacity include, without limitation, those described in U.S. Pat. No. 6,168,778 and U.S. Pat. No. 6,147,204, the compound EYE001 (formerly known as NX1838) which is a pegylated aptamer that binds with high affinity to the major human VEGF isoform, VEGF variants (U.S. Pat. No. 6,270,933 and International Patent Application WO 99/47677), oligonucleotides with VEGF expression inhibiting capacity blocking the expression thereof, such as antisense RNAs such as those described in U.S. Pat. No. 5,710,136, U.S. Pat. No. 5,661,135, U.S. Pat. No. 5,641,756, U.S. Pat. No. 5,639,872 and U.S. Pat. No. 5,639,736. Other compounds capable of inhibiting VEGF-mediated signaling include ZD6474 (Tuccillo et al., 2005, Clin Cancer Res., 11, 1268-76); COX-2, Tie2 receptor, angiopoietin and neuropilin inhibitors; pigment epithelium-derived factor (PEDF), endostatin, angiostatin, soluble fms-like tyrosine kinase 1 (sFlt1) (Harris et al., 2001, Clin Cancer Res., 7, 1992-1997; U.S. Pat. No. 5,861,484); PTK787/ZK222 584; KRN633 (Maier et al., 2004, Mol Cancer Ther., 3, 1639-1649); VEGF-Trap® (Regeneron) and alpha2-antiplasmin (Matsuno et al, 2003, Blood, 120, 3621-3628). Other group of VEGF inhibitory agents are antibodies or antibody fragments which maintain the antigen-binding capacity, specific against VEGF or any of the members of the same family such as VEGF B, I, C, D; PDGF. Preferred examples of anti-VEGF antibodies include Avastin™ (known as bevacizumab, Genentech) or fragments thereof and Lucentis™ (also known as rhuFAb V2, AMD-Fab; ranibizumab, Genentech).

Additionally, the results obtained by the researchers with respect to the methods for selecting a personalized therapy allow the personalized treatment of a patient with colorectal cancer depending on the aprataxin expression levels in a sample isolated from said patient. Therefore in another aspect, the invention relates to the use of a topoisomerase I inhibitor for the preparation of a drug for treating colorectal cancer in a patient where the patient is selected for said treatment if low APTX expression levels with respect to a reference value are detected in a sample isolated from said patient.

Alternatively, the invention relates to a topoisomerase I inhibitor for use in treating colorectal cancer in a patient where the patient is selected for said treatment if low APTX expression levels with respect to a reference value are detected in a sample isolated from said patient.

Alternatively, the invention relates to a method for treating colorectal cancer in a patient which comprises administering a topoisomerase I inhibitor to said patient where the patient is selected for said treatment if low APTX expression levels with respect to a reference value are detected in a sample isolated from said patient.

In addition, patients having high aprataxin expression levels and who therefore will not respond to the treatment with topoisomerase I inhibitors are candidates to receive alternative therapies suitable for colorectal cancer such as a platinum-based agent, an EGF inhibitor, a VEGF inhibitor or a combination of one or more of the above. Therefore in another aspect, the invention relates to the use of a platinum-based agent, an EGF inhibitor, a VEGF inhibitor or a combination of one or more of the above or for the preparation of a drug for treating colorectal cancer where the patient is selected for said treatment if high APTX expression levels with respect to a reference value are detected in a sample isolated from said patient.

Alternatively, the invention relates to a platinum-based agent, an EGF inhibitor, a VEGF inhibitor or a combination of one or more of the above for use in treating colorectal cancer where the patient is selected for said treatment if high APTX expression levels with respect to a reference value are detected in a sample isolated from said patient.

Alternatively, the invention relates to a method for treating colorectal cancer in a patient which comprises administering a platinum-based agent, an EGF inhibitor, a VEGF inhibitor or a combination of one or more of the above to said patient where the patient is selected for said treatment if high APTX expression levels with respect to a reference value are detected in a sample isolated from said patient.

Topoisomerase I inhibitory compounds, platinum-based agent, EGFR inhibitors and VEGF inhibitors have been described in detail above in relation to the method for designing personalized therapy. In a preferred embodiment, the topoisomerase I inhibitor is irinotecan. In another preferred embodiment, the platinum-based agent is oxaliplatin, the EGFR inhibitor is an EGFR-specific antibody and the VEGF inhibitor is an EGFR-specific antibody.

The topoisomerase I inhibitor, the platinum-based agent, the EGFR inhibitor, the VEGF inhibitor or the combination of one or more of the above can be administered by means of different methods, for example intravenously, intraperitoneally, subcutaneously, intramuscularly, topically, intradermally, orally, intranasally or intrabronchially, and they can be administered locally or systemically or directly to the target site. A review of the different methods for administering active ingredients, excipients to be used and of the methods for preparing them can be found in the Treaty of Galenic Pharmacy, C. Faulí i Trillo, Luzán S, S. A. de Ediciones, 1993 and in Remington's Pharmaceutical Sciences (A. R. Gennaro, Ed.), 20th edition, Williams & Wilkins PA, USA (2000).

The therapeutic agents according to the present invention can be formulated together with an excipient which is acceptable from the pharmaceutical view point. Preferred excipients for use in the present invention include sugars, starches, celluloses, rubbers and proteins. In a particular embodiment, the pharmaceutical composition of the invention will be formulated in a solid (for example tablets, capsules, pills, granules, suppositories, sterile crystalline or amorphous solids which can be reconstituted to obtain liquid forms etc.), liquid (for example solutions, suspensions, emulsions, elixirs, lotions, ointments, etc.) or semisolid (gels, ointments, creams and the like) pharmaceutical dosage form. Examples of pharmaceutically acceptable carriers are known in the state of the art and include phosphate buffered saline solutions, water, emulsions, such as oil/water emulsions, different types of moisturizing agents, sterile solutions, etc. The compositions comprising said carriers can be formulated by conventional methods known in the state of the art.

Pharmaceutical Compositions of the Invention

The authors of the present invention have shown that aprataxin deficient cells are more sensitive to topoisomerase I inhibitor-mediated inhibition (see Example 1 of the present invention). It is thus possible to increase the efficacy of treatments based on inhibiting topoisomerase I by means of the simultaneous administration of aprataxin inhibitory agents. Therefore in another aspect, the invention relates to a composition comprising a topoisomerase I inhibitor and an APTX inhibitor.

As used herein, the term "composition" refers to a mixture of two or more bioactive agents and particularly defines a kit of parts in the sense that the different components can be independently dosed, i.e., simultaneously or at different times. Additionally, the expression also refers to a commercial packaging comprising the components of the composition and, optionally, instructions for the simultaneous, sequential (spaced in time) or separated use. Therefore the different components of the composition can be administered simultaneously or sequentially, i.e., at different times with constant or variable intervals and in the same region or in the different regions of the body. The administration intervals in the case of sequential administration or the administration routes in the case of separated administration are preferably chosen such that the effect of the composition is greater than when each of the components are administered separately. The ratio between the doses of the first and second component may vary according to factors such as the particular disease, age, sex, weight, etc. of the patient. The administration of the composition preferably results in an advantageous effect, specifically, in an increase of the therapeutic effect of the composition with respect to each of the components such that it is possible to achieve the same result with smaller doses of each of the components, thus reducing the side effects. The use of the composition preferably achieves a synergic effect between both components.

Possible topoisomerase I inhibitors useful for the compositions of the present invention are those described above in the context of the first method of the invention. In a preferred embodiment, the topoisomerase I inhibitor is irinotecan.

In the context of the present invention, "aprataxin inhibitors" is understood as the compounds which reduce aprataxin activity, as well as any substance or compound which is capable of preventing or blocking the transcription and translation of aprataxin encoding gene (i.e., prevent or block the expression of said gene), or which is capable of preventing the protein encoded by said gene from performing its function (activity).

By way of illustration, aprataxin expression inhibitory agents suitable for use in the present invention are, for example, antisense oligonucleotides, interfering RNAs (siRNAs), catalytic RNAs or specific ribozymes, RNA with "decoy" activity, i.e., with capacity for specifically binding to a factor (generally protein) important for gene expression, such that the expression of the gene of interest, in this case aprataxin, is inhibited, etc. Likewise, inhibitory agents capable of preventing the protein encoded by said aprataxin encoding gene from performing its function are, for example, protein inhibitory peptides, antibodies specifically directed against the epitopes of the protein essential for performing its function, or against aprataxin, etc.

Therefore, in a particular embodiment of the invention, the inhibitory agent is selected from the group consisting of siRNAs, antisense oligonucleotides, specific ribozymes, antibodies and polypeptides. In a preferred embodiment of the invention, the aprataxin inhibitor is an aprataxin-specific siRNA.

siRNA

Small interfering RNAs or siRNAs are agents capable of inhibiting the expression of a target gene by means of RNA interference. A siRNA can be chemically synthesized, it can be obtained by means of in vitro transcription or can be synthesized in vivo in the target cell. siRNAs typically consist of a double-stranded RNA between 15 and 40 nucleotides long, which can contain an overhang region at 3' and/or 5' of 1 to 6 nucleotides. The length of the overhang region is independent of the total length of the siRNA molecule. siRNAs act by means of post-transcriptional degradation or silencing of the target messenger.

siRNAs can be the so-called shRNA (short hairpin RNA), characterized in that the antiparallel strands forming the siRNA are connected by a loop or hairpin region. shRNAs can be encoded by plasmids or viruses, particularly retroviruses, and be under the control of promoters such as the RNA polymerase III U6 promoter.

The siRNA of the invention are substantially homologous to the mRNA of the gene encoding aprataxin or to the genomic sequence encoding said protein. "Substantially homologous" is understood as having a sequence that is sufficiently complementary or similar to the target mRNA, such that the siRNA is able to cause degradation thereof by RNA interference. The siRNAs suitable for causing said interference include siRNAs formed by RNA and siRNAs containing different chemical modifications such as:

siRNAs in which the bonds between the nucleotides are different from those found in nature, such as phosphorothioate bonds;

conjugates of the RNA strand with a functional reagent, such as a fluorophore;

modifications to the ends of the RNA strands, particularly the 3' end by means of modifying hydroxyl at position 2' with different functional groups;

nucleotides with modified sugars such as O-alkylated moieties at position 2', such as 2'-O-methylribose or 2'-O-fluororibose;

nucleotides with modified bases such as halogenated bases (for example 5-bromouracil and 5-iodouracil), alkylated bases (for example 7-methylguanosine).

The siRNAs and shRNAs of the invention can be obtained using a series of techniques known by the person skilled in the art. The region of the nucleotide sequence used as a basis for designing the siRNAs is not limiting and can contain a region of the coding sequence (between the start codon and stop codon), or it can alternatively contain sequences of the 5' or 3' untranslated region, preferably between 25 and 50 nucleotides in length and at any position downstream with respect to the start codon. One way to design a siRNA involves identifying the AA(N19)TT motifs, where N can be any nucleotide in the sequence encoding aprataxin, and selecting those having a high G/C content. If the motifs are not found, it is possible to identify the NA(N21) motive, where N can be any nucleotide.

Suitable examples of siRNAs for use in the present invention include the siRNA described by Luo et al. (Mol. Cell. Biol, 2004, 24:8356-8365).

Antisense Oligonucleotides

An additional aspect of the invention relates to the use of isolated "antisense" nucleic acids to inhibit the expression, for example, inhibiting the transcription and/or translation of a nucleic acid encoding aprataxin the activity of which is to be inhibited. Antisense nucleic acids can bind to the potential target of the drug by means of conventional base complementarity, or, for example, in the case of binding to double-stranded DNA, through specific interactions in the major groove of the double helix. In general, these methods relate to the range of techniques generally used in the art and include any method which is based on the specific binding to oligonucleotide sequences.

An antisense construct of the present invention can be distributed, for example, as an expression plasmid which, when transcribed in the cell, produces RNA that is complementary to at least one unique part of the cell mRNA that encodes aprataxin. Alternatively, the antisense construct is an oligonucleotide probe generated ex vivo and which, when introduced into the cell, inhibits gene expression by hybridizing with the mRNA and/or genomic sequences of a target nucleic acid. Such oligonucleotide probes are preferably modified oligonucleotides which are resistant to endogenous nucleases, for example exonucleases and/or endonucleases, and are therefore stable in vivo. Exemplary nucleic acid molecules for use as antisense oligonucleotides include DNA analogs of phosphoramidate, phosphothionate and methylphosphonate (also see, for example, U.S. Pat. Nos. 5,176, 996, 5,264,564 and 5,256,775). Additionally, for a review of general approaches for constructing oligomers useful in antisense therapy, see, for example, Van der Krol et al., BioTechniques 6: 958-976, 1988; and Stein et al., Cancer Res 48: 2659-2668, 1988.

Regarding the antisense oligonucleotide, the oligodeoxyribonucleotide regions derived from the translation start site, for example, between −10 and +10 of the target gene, are preferred. Antisense approaches involve designing oligonucleotides (either DNA or RNA) complementary to the mRNA encoding the target polypeptide. Antisense oligonucleotides will bind to mRNA transcripts and prevent translation.

Oligonucleotides complementary to the 5' end of the mRNA, for example, the untranslated 5' sequence until and including the start codon AUG should work in the most efficient manner to inhibit translation. However, it has been recently shown that the sequences complementary to the 3' untranslated sequences of the mRNAs are also effective for inhibiting mRNAs translation (Wagner, Nature 372: 333, 1994). Therefore, oligonucleotides complementary to either the untranslated non-coding 5' or 3' regions of a gene in an antisense approach could be used for inhibiting the translation of that mRNA. The oligonucleotides complementary to the untranslated 5' region of the mRNA must include the complement of the start codon AUG. The oligonucleotides complementary to the coding regions of the mRNA are less effective translation inhibitors but could also be used according to the invention. If they are designed to hybridize with the 5' or 3' or coding region of the mRNA, the antisense nucleic acids must be at least 6 nucleotides long and preferably less than about 100, and more preferably less than about 50, 25, 17 or 10 nucleotides long.

in vitro studies must preferably be conducted to quantify the capacity of the antisense oligonucleotides to inhibit gene expression. These studies preferably use controls that distinguish between antisense gene inhibition and nonspecific biological effects of the oligonucleotides. It is also preferred that those studies compare the target RNA or protein levels with the RNA or protein level of an internal control. The results obtained using antisense oligonucleotides can be compared with those obtained using a control oligonucleotide. It is preferred that the control oligonucleotide is approximately the same length as the oligonucleotide to be assayed and that the oligonucleotide sequence differs from the antisense sequence by no more than that necessary to prevent specific hybridization to the target sequence.

The antisense oligonucleotides can be single-stranded or double-stranded DNA, RNA or chimeric mixtures or derivatives or modified versions thereof. The oligonucleotide can be modified in the base group, in the sugar group or in the phosphate backbone, for example, to improve the stability of the molecule, its hybridization capacity, etc. The oligonucleotide can include other groups bound thereto, such as peptides (for example to direct them to host cell receptors) or agents to facilitate transport across the cell membrane (see, for example, Letsinger et al., Proc. Natl. Acad. Sci. USA 86: 6553-6556, 1989; Lemaitre et al., Proc. Natl. Acad. Sci. 84: 648-652, 1987; PCT Publication No. WO88/09810) or the blood-brain barrier (see, for example, PCT Publication No. WO89/10134), or intercalating agents (See, for example, Zon, Pharm. Res. 5: 539-549, 1988). For this purpose, the oligonucleotide can be conjugated to another molecule, for example, a peptide, a carrier agent, a hybridization-triggered cleavage agent, etc.

The antisense oligonucleotides can comprise at least one modified base group. The antisense oligonucleotide can also comprise at least one modified sugar group selected from the group including, but not limited to, arabinose, 2-fluoroarabinose, xylulose, and hexose. The antisense oligonucleotide can also contain a backbone similar to neutral peptide. Such molecules are called peptide nucleic acid oligomers (PNA) and are described, for example, in Perry-O'Keefe et al., Proc. Natl. Acad. Sci. U.S.A. 93: 14670, 1996, and in Eglom et al., Nature 365: 566, 1993.

In yet another embodiment, the antisense oligonucleotide comprises at least one modified phosphate backbone.

In still another embodiment, the antisense oligonucleotide is an alpha-anomeric oligonucleotide.

While antisense oligonucleotides complementary to the coding region of the target sequence of mRNA can be used, those complementary to the untranslated transcribed region can also be used.

In some cases it may be difficult to achieve intracellular concentrations of antisense oligonucleotide sufficient to suppress endogenous mRNA translation. Therefore, a preferred approach uses a recombinant DNA construct in which the antisense oligonucleotide is placed under the control of a strong pol III or pol II promoter.

Alternatively, expression of the target gene can be reduced by directing deoxyribonucleotide sequences complementary to the regulatory region of the gene (i.e., promoter and/or enhancers) in order to form triple-helix structures preventing gene transcription in target cells in the body (see, in general, Helene, Anticancer Drug Des. 6(6): 569-84, 1991).

In certain embodiments, the antisense oligonucleotides are antisense morpholines.

DNA Enzymes

Another aspect of the invention relates to the use of DNA enzymes to inhibit the expression of the gene encoding the aprataxin of the invention. DNA enzymes incorporate some of the mechanistic features of both the antisense technologies and ribozyme technologies. DNA enzymes are designed such that they recognize a target sequence of the particular nucleic acid, similar to the antisense oligonucleotide, however, like the ribozyme, they are catalytic and specifically cleave the target nucleic acid.

Ribozymes

Ribozyme molecules designed to catalytically cleave target mRNA transcripts can also be used to prevent translating the mRNAs encoding aprataxin the activity of which is to be inhibited. Ribozymes are enzymatic RNA molecules capable of catalyzing the specific RNA cleavage (for a review see Rossi, Current Biology 4: 469-471, 1994.). The mechanism of action of the ribozyme involves specific sequence hybridization of the ribozyme molecule to a complementary target RNA followed by an endonucleotic cleavage. The composition of the ribozyme molecules preferably includes one or more sequences complementary to the target mRNA and the well-known sequence responsible for the mRNA cleavage or a functionally equivalent sequence (see, for example, U.S. Pat. No. 5,093,246).

The ribozymes used in the compositions of the present invention include hammerhead ribozymes, RNA endoribonucleases, (hereinafter "Cech type ribozymes") (Zaug et al., Science 224:574-578, 1984.).

Ribozymes can be made up of modified oligonucleotides (for example to improve stability, targeting, etc.) and they must be distributed to cells expressing the target gene in vivo. A preferred method of distribution involves using a DNA construct "encoding" the ribozyme under the control of a strong constitutive pol III or pol II promoter, such that transfected cells will produce sufficient amounts of the ribozyme to destroy target endogenous messengers and inhibit translation. Since ribozymes are catalytic unlike other antisense molecules, a smaller intracellular concentration is required for them to be effective.

Inhibitory Peptides

As used herein, the term "inhibitory peptide" refers to those peptides capable of binding to apratoxin and inhibiting its activity as has been described above, i.e., preventing the apratoxin from activating gene transcription.

Inhibitory Antibodies

"Inhibitory antibody" is understood in the context of the present invention as any antibody capable of binding to apratoxin in a specific manner and inhibiting one or more functions of apratoxin, preferably those related to transcription. An "inhibitory antibody" is also any antibody that is capable of binding to apratoxin in a specific manner and blocking apratoxin oligomerization or apratoxin binding sites with other proteins. The antibodies can be prepared using any methods known by the person skilled in the art, some of which have been described above. Once the antibodies with apratoxin binding capacity have been identified, those that are capable of inhibiting the activity of this protein will be selected using inhibitory agent identification assay (see, for example, Metz, S. et al. J. Biol. Chem. 283:5985-5995, 2008.).

Other Apratoxin Activity Inhibitory Compounds

Other compounds with capacity of inhibiting the expression of an apratoxin include aptamers and spiegelmers, which are single- or double-stranded D or L nucleic acids which specifically bind to the protein, resulting in a modification of the biological activity thereof. Aptamers and spiegelmers have a length of between 15 and 80 nucleotides, and preferably between 20 and 50 nucleotides.

The compositions of the invention can be used in medicine for treating cancer and particularly colorectal cancer. Therefore in another aspect, the invention relates to a composition of the invention for use in medicine.

In another aspect, the invention relates to the use of a composition comprising a topoisomerase I inhibitor and an aprataxin inhibitor for the preparation of a drug for treating cancer. Alternatively, the invention relates to a composition comprising a topoisomerase I inhibitor and an aprataxin inhibitor for use in treating cancer. Alternatively, the invention relates to a method for treating cancer in a subject which comprises administering a composition comprising a topoisomerase I inhibitor and an aprataxin inhibitor to said subject.

The types of formulation and administration routes of the compositions of the invention have been described en in detail above and are essentially the same as those used for each of the components used separately.

The compositions of the invention are suitable for treating different types of cancer including, without limitation, those described above in the context of the first method of the invention. In a preferred embodiment, the cancer is colorectal cancer.

The invention is illustrated below based on the following examples which are provided by way of illustration and are not limiting to the scope of the invention.

EXAMPLES

Materials and Methods

Characterization of Sensitivity to Camptothecin.

Chicken parental B cell line DT40, a sub-line where ATPX was interrupted by means of homologous recombination and a derivative line where APTX was re-introduced in the knockout cells were used (Abel I, et al., Nature 2006; 443: 713-6). Camptothecin-induced apoptosis was evaluated as has been previously described (Arango D, et al., Cancer Res 2001; 61: 4910-5; Arango D, et al., Br J Cancer 2003; 89: 1757-65). Briefly, $2.5\times10^5$ cells were seeded by triplicate in 6-well Falcon plates (Becton Dickinson) and were left to adhere for 24 hours before sucking out the medium and changing it with fresh medium containing 0, 15 or 25 nM camptothecin (Calbiochem, San Diego, Calif.). After 72 hours of treatment, both the adhered cells and those that floated were collected, they were washed two times with 2 ml of PBS, and resuspended in PBS containing 50 μg/ml propidium iodide, 0.1% sodium citrate, and 0.1% Triton X-100. The cells were stained overnight at 4° C. and the DNA content was analyzed using a cell separator (FACSCalibur; Becton Dickinson). The cell debris were discarded, and the proportion of cells with subdiploid DNA content typical of apoptotic cells was quantified using WinList 2.0 (Verity Software House, Inc.). All the experiments were carried out in triplicate, and the mean from three independent experiments is shown.

Patients

A total of 135 patients with metastatic colorectal cancer receiving irinotecan-based chemotherapy in Hospital Universitario Vall d'Hebron were included in the study. Table 1 summarizes the clinicopathological information of the patients. The response to the chemotherapeutic treatment was evaluated by means of computerized axial tomography (CAT) and a response was considered complete when the complete disappearance of metastatic lesions was observed. The patients with stable disease showed between 30% drop and 20% increase in the sum of lesion diameter. A lesion size reduction observed by CAT greater than 30% or an increase above 20% were considered as partial response or progressive disease, respectively. The study was conducted according to the research protocols approved by the Clinical Research Ethics Committee.

TABLE 1

Clinical characteristics of the 135 patients in the set used in this study.

| | Total | Low aprataxin | High aprataxin | p value* |
|---|---|---|---|---|
| Sex - no. (%) | | | | |
| Man | 50 (37.0) | 20 (30.3) | 30 (43.5) | 0.15[1] |
| Woman | 85 (63.0) | 46 (69.7) | 39 (56.5) | |
| Age (years) | 64.2 | 63.0 | 61.9 | 0.78[2] |
| Irinotecan protocol - no. (%) | | | | |
| CPT11 monotherapy | 60 (46.9) | 23 (37.1) | 37 (56.1) | 0.1[3] |
| FOLFIRI monotherapy | 41 (32.0) | 26 (41.9) | 15 (22.7) | |
| FOLFIRI + Bevacizumab | 8 (6.3) | 4 (6.5) | 4 (6.2) | |
| FOLFIRI + Cetuximab | 19 (14.8) | 9 (14.5) | 10 (15.2) | |
| Degree of differentiation of tumor - no. (%) | | | | |
| Well-differentiated | 13 (10.4) | 7 (11.7) | 6 (9.2) | 0.44[3] |

TABLE 1-continued Clinical characteristics of the 135 patients in the set used in this study.

|  | Total | Low aprataxin | High aprataxin | p value* |
|---|---|---|---|---|
| Moderately-differentiated | 74 (59.2) | 38 (63.3) | 36 (55.4) | |
| Poorly-differentiated | 38 (30.4) | 15 (25) | 23(35.4) | |
| Objective response | | | | |
| Full response | 9 (7.7) | 7 (11.9) | 2 (3.5) | 0.13[3] |
| Partial response | 30 (25.9) | 17 (28.8) | 13 (22.8) | |
| Stable disease | 29 (25) | 16 (27.1) | 13 (22.8) | |
| Progressive disease | 48 (41.4) | 19 (32.2) | 29 (50.9) | |
| Overall survival median - (months) | 26.3 | 36.7 | 19 | 0.008[4] |

*p values calculated using Fisher's Exact Test (1), Mann-Whitney Test (2), Chi-squared Test (3) or Log-rank Test (4) for comparing high and low aprataxin.
FOLFIRI: Irinotecan with fluorouracil (5FU) and folinic acid.

Tissue Microarrays and Immunohistochemical Analysis

After the histological examination of tumor sample sections stained with hematoxylin and eosin and fixed with formalin embedded in paraffin, areas containing a large proportion of tumor cells were selected from the 135 patients. Cores of 1.2 mm of tumor samples from each patient were arranged in duplicate in a new paraffin block using an apparatus for preparing tissue matrices from Beecher Instruments (Beecher Instruments, Silver Spring, Md.).

4 µm unstained sections of the tissue microarrays were mounted on slides coated with 3-aminopropyl-triethoxy-silane (Sigma, St. Louis, Mo., USA). The sections were deparaffinized in xylene and rehydrated by means of a gradual series of alcohol and distilled water. The antigen was recovered with preheated 10 mM pH=6 citrate buffer for 20 minutes at 95° C. For the immunohistochemical analysis, the commercial Novolink polymer detection system was used according to the manufacturer's instructions (Novocastra Laboratories; Newcastle, UK). A rabbit anti-aprataxin polyclonal antibody made against the C-terminus end of human aprataxin was used at a dilution 1:100 (4° C. overnight; Aviva Systems Biology Corp.; San Diego, Calif.). The staining was viewed using a solution of 3,3'-diaminobenzidine (DAB) and the sections were counter stained in Mayer's hematoxylin, washed in water, dehydrated through a series of ethanol solution, clarified in xylene and mounted. The aprataxin levels were evaluated without knowing the clinical data. A semi-quantitative scale from 0 to 3 was used to measure the staining intensity. The absence of aprataxin staining was graded as 0 and the low, moderate and high aprataxin levels were graded as 1, 2, and 3, respectively (see FIG. 2A-D). The mean grading of samples in duplicate was used in subsequent analysis.

Statistical Analysis

Survival curves were plotted using Kaplan and Meier method and the survival differences were evaluated using log-rank test. Cox's proportional hazard model was used to evaluate the simultaneous contribution of the following covariables in the overall survival: sex, age, histological grade, and tumor aprataxin levels. Fisher's exact test, Chi-squared test and Mann-Whitney test were used to evaluate the differences between clinicopathological parameters in patients with high and low aprataxin levels (see Table 1). It was considered that the p values of less than 0.05 indicated statistic significant.

Example 1

Aprataxin Regulates the Sensitivity to CPT

Figure 1:
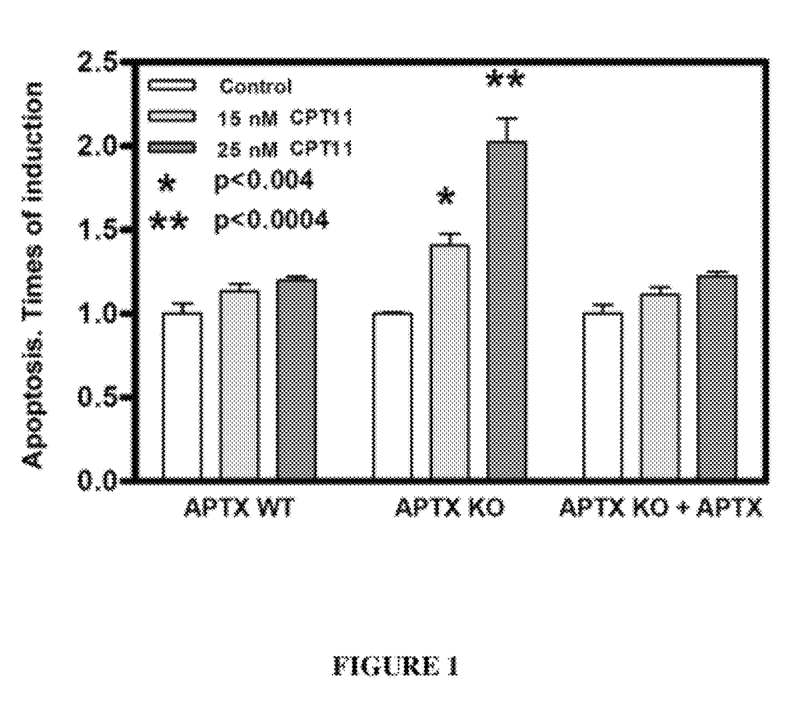

It was previously determined that the aprataxin expression at the mRNA level is significantly associated (apoptotic response at 72 hour exposure to 100 mM CTP; Spearman R=0.54 p=0.0022) with the sensitivity of a panel of colorectal cancer cell lines to camptothecin (CPT), an irinotecan analogue which is metabolized into the same active component, SN38 (Mariadason J M, et al., Cancer Res 2003; 63: 8791-812). A manipulated in vitro system where both APTX alleles were inactivated by means of homologous recombination was used herein to directly evaluate the role of aprataxin in the sensitivity to CPT (Abel I, et al., Nature 2006; 443: 713-6). FIG. 1 shows that the treatment of the parental cells DT40 with 15-25 nM CTP for 72 hours caused a modest apoptosis induction. However, the directed inactivation of APTX significantly sensitized (p<0.004) the cells to the treatment with CPT. Furthermore, the reintroduction of APTX in APTX knock-out cells completely reestablished the CPT resistant phenotype of the parental cells DT40, demonstrating that aprataxin directly regulates the sensitivity to CPT (FIG. 1).

Example 2

Low Tumor Aprataxin Levels Predict a Good Response to Irinotecan

Figure 2:
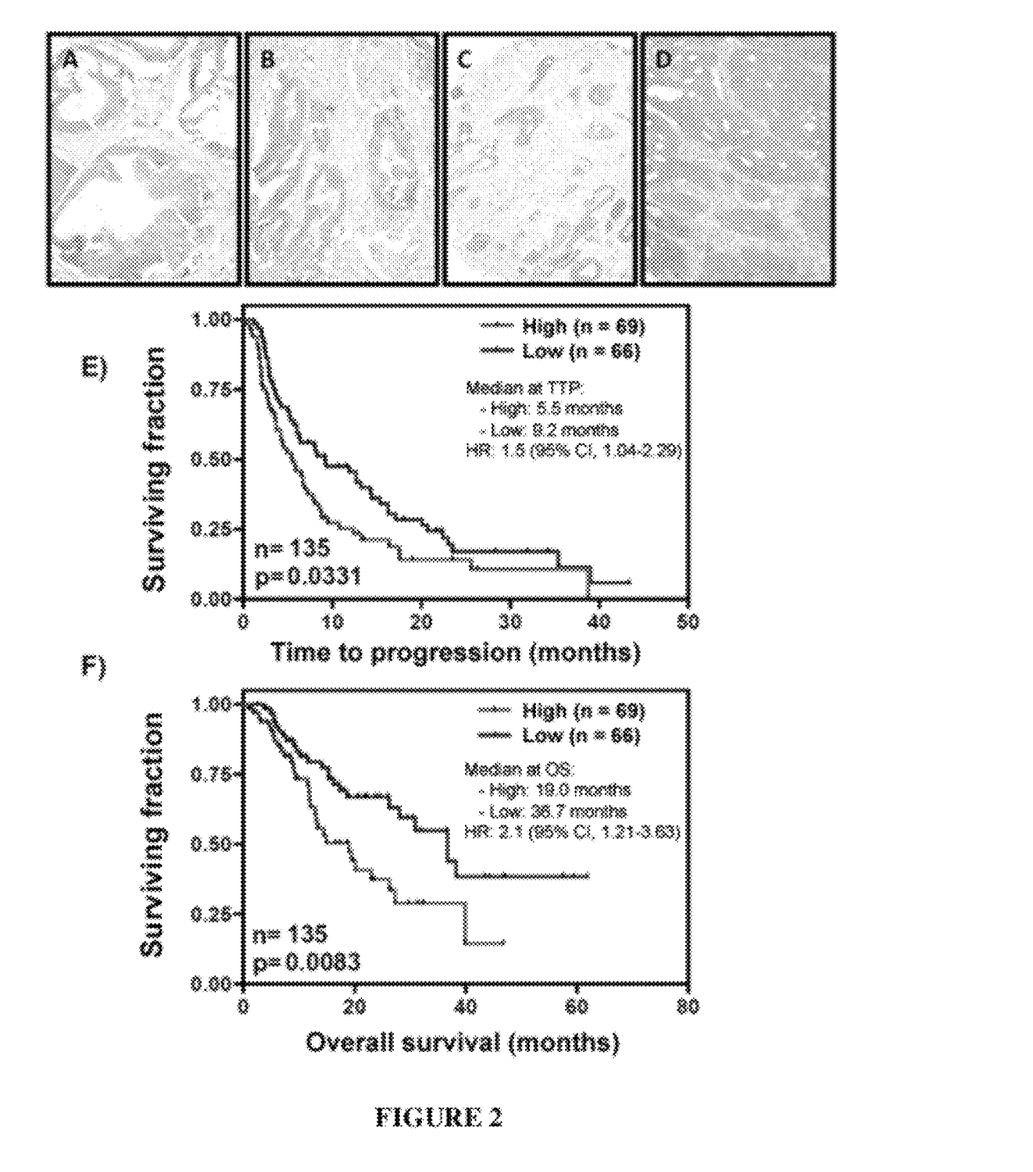
FIG. 2 shows the tumor aprataxin levels and the survival of patients with advanced colorectal cancer who received irinotecan-based treatment. The immunohistochemical staining of colorectal tumors showed an expression gradient, with some tumors which did not have detectable aprataxin expression levels (A), high aprataxin expression levels (D) or intermediate aprataxin expression levels (B-C). The time to progression (E) and the overall survival (F) are shown according to the levels of aprataxin protein (Kaplan-Meier graphs). The p values of the logarithmic order are shown.

Next the value of tumor aprataxin levels as a marker of response to CPT11 (irinotecan) was to be investigated. For this purpose, a set of patients with metastatic colorectal cancer receiving irinotecan-based treatment (see table I) were used. A tissue micromatrix (TMA) containing samples in duplicate of 135 of these patients was constructed. Aprataxin expression levels in these tumors were evaluated by means of immunohistochemical techniques and an expression gradient was observed, which varied from the complete absence (FIG. 2A) to high tumor aprataxin levels (FIG. 2D). The time to progression (TTP) for patients with moderate or high tumor aprataxin levels was significantly shorter (log-rank test, p=0.03) than in patients with the absence or low aprataxin levels (TTP median of 5.5 and 9.2 months, respectively; hazard ratio of 1.5; 95% CI, 1.04-2.29; FIG. 2E). The absence of/low aprataxin was also associated with significantly longer overall survival (log-rank test, p=0.008) in patients with colorectal cancer who received irinotecan-based chemotherapy (TTP median of 19 and 36.7 months, respectively; hazard ratio of 2.1; 95% CI, 1.21-3.63) indicating a better response to treatment with irinotecan (FIG. 2F).

The invention claimed is:
1. A method of treating colorectal cancer comprising
  (i) determining the levels of APTX in a sample isolated from a patient having colorectal cancer,
  (ii) selecting a patient for said treatment if low APTX expression levels with respect to a reference value are detected in said sample, and
  (iii) administering a topoisomerase I inhibitor to said patient, wherein the topoisomerase I inhibitor is selected from the group consisting of topotecan, gimatecan, irinotecan, camptothecin, SN 38 and its analogues, 9-nitrocamptothecin and the macromolecular camptothecin conjugate PNU-166148, 10-hydroxycamptothecin acetate salt, idarubicin hydrochloride, irinotecan hydrochloride; teniposide, topotecan hydrochloride, doxorubicin, epirubicin hydrochloride, mitoxantrone hydrochloride and daunorubicin hydrochloride.

2. A method of treating colorectal cancer according to claim 1, wherein said topoisomerase I inhibitor is irinotecan.

3. A method of treating colorectal cancer comprising
   (i) determining the levels of APTX in a sample isolated from a patient having colorectal cancer,
   (ii) selecting a patient for said treatment if high APTX expression levels with respect to a reference value are detected in said sample, and
   (iii) administering a platinum-based agent, an EGFR inhibitor, a VEGF inhibitor or a combination of one or more of the foregoing to said patient, wherein the EGFR inhibitor is an EGFR-specific antibody and/or the VEGF inhibitor is an VEGF-specific antibody.

4. A method of treating colorectal cancer according to claim 3, wherein the platinum-based agent is oxaliplatin.

5. The method according to claim 1 further comprising administering 5-fluorouracil to the patient.

6. The method according to claim 2 further comprising administering 5-fluorouracil to the patient.

\* \* \* \* \*

UNITED STATES PATENT AND TRADEMARK OFFICE
CERTIFICATE OF CORRECTION

PATENT NO. : 9,028,831 B2
APPLICATION NO. : 13/393215
DATED : May 12, 2015
INVENTOR(S) : Diego Arango Del Corro It is certified that error appears in the above-identified patent and that said Letters Patent is hereby corrected as shown below:

Title Page, Item 30: "200901817" should be -- P200901817 --.

Title Page, Item 56: under OTHER PUBLICATIONS, the following 3 references cited were omitted:

Pommier (Topoisomerase I inhibitors: camptothecins and beyond, 2006, vol 6, pg 789-802)

Mosesso et al (The novel human gene aprataxin is directly involved in DNA single-strand-break repair, 2005, Cell. and Mol. LifeSci., vol 62, pg 485-491)

Luo et al (A New XRCC1-Containing Complex and Its Role in Cellular Survival of Methyl Methanesulfonate Treatment, 2004, Mol and Cell Bio, Vol 24, pg 8356-8365)

In the Specification

Column 2, line 61-62: "CPT for hours" should be -- CPT for 72 hours --.

Column 6, line 65: "between and 4)" should be -- between 0 and 4) --.

Column 8, line 39: "SN and its analogues" should be -- SN 38 and its analogues --.

Column 17, line 67: "Abel I" should be -- Ahel I --.

Column 20, line 11: "J M" should be -- JM --.

Column 20, line 15: "Abel I" should be -- Ahel I --.

Signed and Sealed this
Twenty-third Day of June, 2015

Michelle K. Lee
*Director of the United States Patent and Trademark Office*